US010857191B2

(12) United States Patent
Levenson et al.

(10) Patent No.: US 10,857,191 B2
(45) Date of Patent: Dec. 8, 2020

(54) SANDALWOOD OIL AND ITS USES RELATED TO ORAL MUCOSITIS

(71) Applicant: Santalis Pharmaceuticals, Inc., San Antonio, TX (US)

(72) Inventors: Corey Levenson, San Antonio, TX (US); Paul Castella, San Antonio, TX (US); Ian Clements, San Antonio, TX (US)

(73) Assignee: SANTALIS PHARMACEUTICALS, INC., San Antonio, TX (US)

( * ) Notice: Subject to any disclaimer, the term of this patent is extended or adjusted under 35 U.S.C. 154(b) by 0 days.

(21) Appl. No.: 15/766,076

(22) PCT Filed: Oct. 6, 2016

(86) PCT No.: PCT/US2016/055766
§ 371 (c)(1),
(2) Date: Apr. 5, 2018

(87) PCT Pub. No.: WO2017/062631
PCT Pub. Date: Apr. 13, 2017

(65) Prior Publication Data
US 2019/0209630 A1 Jul. 11, 2019

Related U.S. Application Data

(60) Provisional application No. 62/238,449, filed on Oct. 7, 2015.

(51) Int. Cl.
*A61K 36/185* (2006.01)
*A61Q 11/00* (2006.01)
*A61K 8/92* (2006.01)
*A61K 9/00* (2006.01)
*A61K 47/10* (2017.01)
*A61K 47/26* (2006.01)
*A61K 45/06* (2006.01)

(52) U.S. Cl.
CPC ............ *A61K 36/185* (2013.01); *A61K 8/922* (2013.01); *A61K 9/006* (2013.01); *A61K 45/06* (2013.01); *A61K 47/10* (2013.01); *A61K 47/26* (2013.01); *A61Q 11/00* (2013.01)

(58) Field of Classification Search
None
See application file for complete search history.

(56) References Cited

U.S. PATENT DOCUMENTS

| 5,520,918 | A | 5/1996 | Smith |
| 5,653,970 | A | 8/1997 | Vermeer |
| 5,693,327 | A | 12/1997 | Shah |
| 5,944,754 | A | 8/1999 | Vacanti |
| 6,132,756 | A | 10/2000 | Haque et al. |
| 6,368,639 | B1 | 4/2002 | Farooqi et al. |
| 6,406,706 | B1 | 6/2002 | Haque et al. |
| 6,576,269 | B1 | 6/2003 | Korneyev |
| 6,578,571 | B1 | 6/2003 | Watt |
| 7,858,126 | B2 | 12/2010 | Singh et al. |
| 2004/0123974 | A1 | 7/2004 | Marler et al. |
| 2005/0158258 | A1 | 7/2005 | Fisher |
| 2006/0058238 | A1 | 3/2006 | Laurent-Applegate et al. |
| 2007/0166275 | A1 | 7/2007 | Gan et al. |
| 2009/0036413 | A1* | 2/2009 | McAnalley ............ A61K 9/06 514/163 |
| 2009/0047342 | A1 | 2/2009 | Forbes et al. |
| 2009/0047372 | A1 | 2/2009 | Miller |
| 2009/0068128 | A1 | 3/2009 | Waddington |
| 2009/0274677 | A1 | 11/2009 | Isaacs et al. |
| 2010/0029766 | A1 | 2/2010 | Barclay et al. |
| 2010/0226983 | A1 | 9/2010 | Sutcliffe et al. |
| 2010/0303854 | A1 | 12/2010 | Hines et al. |
| 2013/0005830 | A1* | 1/2013 | Clements ............ A61K 36/185 514/729 |
| 2014/0154342 | A1 | 6/2014 | Clements et al. |
| 2016/0008415 | A1 | 1/2016 | Clements et al. |
| 2016/0184374 | A1 | 6/2016 | Clements et al. |
| 2018/0042974 | A1 | 2/2018 | Clements et al. |

FOREIGN PATENT DOCUMENTS

| AU | 2011223758 | 10/2012 |
| AU | 2014243923 | 10/2015 |
| AU | 2011223758 | 3/2017 |
| AU | 2017201019 | 3/2017 |
| AU | 2016336518 | 4/2018 |
| CA | 2791897 | 9/2011 |
| CA | 2905034 | 10/2014 |
| CA | 3000854 | 4/2017 |
| CN | 101370508 | 2/2009 |
| CN | 103181937 | 7/2013 |
| CN | 103796650 | 5/2014 |
| EP | 0420630 | 4/1991 |
| EP | 1059086 | 12/2000 |

(Continued)

OTHER PUBLICATIONS

Effective Ingredients of Cosmetics, Skin Care, New Cosmetic Handbook, Nippon Chemicals Sales, Oct. 30, 2006, pp. 559-563.
U.S. Appl. No. 13/582,133, Examiner's Answer to Appeal Brief dated May 29, 2015, 23 pages.
U.S. Appl. No. 13/582,133, Notice of Panel Decision dated Oct. 29, 2014, 2 pages.
U.S. Appl. No. 13/582,133, Restriction Requirement dated Jun. 13, 2013, 10 pages.
U.S. Appl. No. 14/235,387 Advisory Action dated Mar. 24, 2016, 3 pages.
U.S. Appl. No. 14/773,127, Notice of Allowance dated Aug. 7, 2017, 11 pages.

(Continued)

*Primary Examiner* — Celeste A Roney
(74) *Attorney, Agent, or Firm* — Kilpatrick Townsend & Stockton LLP

(57) ABSTRACT

Provided herein are methods of using therapeutically effective compositions of sandalwood oil to treat oral mucositis.

10 Claims, No Drawings

(56) References Cited

FOREIGN PATENT DOCUMENTS

| | | |
|---|---|---|
| EP | 1402785 | 3/2004 |
| EP | 2542251 | 1/2013 |
| EP | 2542251 | 9/2013 |
| EP | 2736504 | 6/2014 |
| EP | 2736504 | 3/2015 |
| EP | 2968136 | 1/2016 |
| GB | 2309902 | 8/1997 |
| HK | 1218391 | 2/2017 |
| IN | 8199DELNP2012 | 3/2014 |
| JP | 2001322943 | 11/2001 |
| JP | 2006124296 | 5/2006 |
| JP | 2009057325 | 3/2009 |
| JP | 2013521299 | 6/2013 |
| JP | 2014521655 | 8/2014 |
| JP | 2016513650 | 5/2016 |
| JP | 5972797 | 8/2016 |
| KR | 1020130006639 | 1/2013 |
| KR | 101842289 | 3/2018 |
| MX | 2012010185 | 2/2013 |
| MX | 350392 | 9/2017 |
| WO | 03059424 | 7/2003 |
| WO | 2004018026 | 3/2004 |
| WO | 2007084998 | 7/2007 |
| WO | 2009017708 | 2/2009 |
| WO | 2010087964 | 8/2010 |
| WO | 2010091415 | 8/2010 |
| WO | 2011002929 | 1/2011 |
| WO | 2011109411 A2 | 9/2011 |
| WO | 2011109411 A9 | 1/2012 |
| WO | 2012059874 | 5/2012 |
| WO | 2013016656 | 1/2013 |
| WO | 2013112582 | 8/2013 |
| WO | 2014121411 | 8/2014 |
| WO | 2014160279 | 10/2014 |
| WO | WO-2016106313 A1 * | 6/2016 ............. A61Q 11/00 |
| WO | 2017062631 | 4/2017 |

OTHER PUBLICATIONS

U.S. Appl. No. 14/773,127 Restriction Requirement dated Jul. 14, 2016, 8 pages.
U.S. Appl. No. 15/469,997 Restriction Requirement dated Nov. 22, 2017, 5 pages.
Australian Application No. 2011223758, First Examiner Report dated Jan. 27, 2015, 4 pages.
Australian Application No. 2011223758, Notice of Acceptance dated Nov. 3, 2016, 2 pages.
Australian Application No. 2011223758, Second Examiner Report dated Sep. 1, 2016, 3 pages.
Australian Application No. 2012286671, First Examiner Report dated Jul. 20, 2016, 3 pages.
Australian Application No. 2017201019, First Examination Report dated Nov. 29, 2017, 5 pages.
Chinese Application No. 201280044415.8, Notice of Decision to Grant dated Oct. 11, 2017, 2 pages.
European Application No. 11751210.3, Communication pursuant to Rule 114(2) EPC including third party observations under Article 115 EPC dated Sep. 10, 2013, 9 pages.
European Application No. 11751210.3, Extended European Search Report dated Aug. 22, 2013, 10 pages.
European Application No. 12818159.1, Extended European Search Report dated Feb. 3, 2015, 7 pages.
European Application No. 14775788.4, Extended European Search Report dated Aug. 19, 2016, 6 pages.
European Application No. 16854327.0, Extended European Search Report dated May 14, 2019, 7 pages.
Indian Application No. IN8199/DELNP/2012, First Examination Report dated May 29, 2013, 4 pages.
Japanese Application No. 2012-556177, Notice of Allowance dated Jun. 15, 2016, 3 pages.
Korean Application No. 10-2012-7025564, Notice of Decision to Grant dated Dec. 21, 2017, 2 pages.
Mexican Application No. MX/a/2012/010185, Notice of Allowance dated Jun. 27, 2017, 2 pages.
International Application No. PCT/US2011/026706, International Preliminary Report on Patentability dated Sep. 13, 2012, 5 pages.
International Application No. PCT/US2011/026706, Written Opinion dated Nov. 24, 2011, 3 pages.
International Application No. PCT/US2012/048599, International Preliminary Report on Patentability dated Feb. 6, 2014, 6 pages.
International Application No. PCT/US2012/048599, International Search Report and Written Opinion dated Nov. 15, 2012, 8 pages.
International Application No. PCT/US2014/026219, International Preliminary Report on Patentability dated Sep. 24, 2015, 8 pages.
International Application No. PCT/US2014/026219, International Search Report and Written Opinion dated Jul. 10, 2014, 11 pages.
International Application No. PCT/US2016/055766, International Preliminary Report on Patentability dated Apr. 19, 2018, 6 pages.
International Application No. PCT/US2016/055766, International Search Report and Written Opinion dated Dec. 8, 2016, 8 pages.
Madhana Kameswara Thylam, Key Attributes to TKDL, 4 pages.
Pharmaceutical Composition for Treating Helicobacter Pylon Infectious Disease such as Duodenal Ulcers, Gastric Ulcers, Gastritis and Stomach Cancer, Contains Sandalwood Component as Active Ingredient, Database WPI Week 200636 Thomson Scientific, London, GB, AN 2006-347100 XP002707361, & JP 2006124296 A, May 18, 2006, 3 pages.
Product Catalogue, Aloe Vera Cosmetics Australia Pty Ltd, Available online at http://www.aloeveracosmetics.com/au/pdf/ACVA-Catalogue-2010.pdf, 22 pages.
Rasatantrasarah Evam Siddhaprayogasamgraha, Krishan Gopal Ayurveda Bhawan, Edn 8th, Part II, 1990, 1 page.
ViroXis Science, Available online at http://www.viroxis.com/science.html, 2012, 2 pages.
Akae et al., Skin External Preparation as a Medicine, Fragrance Journal, vol. 13, No. 2, Mar. 5, 1985, pp. 91-94.
Arzani, Qaraabaadeen Qaadre (17'h century AD), Ahmadi Publication, Delhi, 1968, 2 pages.
Banerjee et al., Modulatory Influence of Sandalwood Oil on Mouse Hepatic Glutathione S-Transferase Activity and Acid Soluble Sulphydryl Level, Cancer Letters, vol. 68, 1993, pp. 105-109.
Boris et al., Cytotoxic Properties of Selected Sesquiterpene Alcohols on Human Cervix Carcinoma Cell Lines, Journal of Essential Oil Bearing Plants, vol. 14, No. 3, 2011, pp. 316-319.
Burdock et al., Safety Assessment of Sandalwood Oil (*Santalum album* L.), Food and Chemical Toxicology, vol. 46, 2008, pp. 421-432.
Duprez et al., Overexpression of BMP-2 and BMP-4 Alters the Size and Shape of Developing Skeletal Elements in the Chick Limb, Mechanisms of Development, vol. 57, 1996, pp. 145-157.
Dwivedi et al., Chemopreventive Effects of Sandalwood Oil on Skin Papillomas in Mice, European Journal of Cancer Prevention, vol. 6, No. 4, Aug. 1997, pp. 399-401.
Erligmann, Sandalwood Oils, The International Journal of Aromatherapy, vol. 11, No. 4, 2001, pp. 186-192.
Gasena, 12th Century Khemraj Shrikrishna Das Prakashan, TKOL Formulation IOAK11/3505, Edited by Shankar Ialji Jain, Bombay, 1996, 2 pages.
Haibin, A Medicated Core of Bra Having Anticancer and Breast Beautifying Effects and its Preparation Method, TCM/SIPO, XP-002707360, Sep. 15, 1992, 4 pages.
Hayes et al., Toxicity of Australian Essential Oil Backhousia Citriodora (*Lemon myrtle*). Part 1. Antimicrobial Activity and in Vitro Cytotoxicity, Food and Chemical Toxicology, vol. 40, 2002, pp. 535-543.
Hettiarachchi et al., Western Australian Sandalwood Seed Oil: New Opportunities, Lipid Technology, vol. 22, No. 2, Feb. 2010, pp. 27-29.
Kaur et al., Skin Cancer Chemopreventive Agent; A•Santalol, Induces Apoptotic Death of Human Eptdermmd Carcmoma A431 Cells Vaa Caspase Activation Together with Dissipation of Mitochondrial Membrane Potential and Cytochrome C Release, Carcinogenesis, vol. 26, No. 2, 2005, pp. 369-380.

(56) References Cited

OTHER PUBLICATIONS

Khan, Ikseer Azam, 19th century AD, Matba Nizami Kanpur, vol. IV, Formulation ID: BA4/1854B, Marham Baraa-e-Sartaan, 1872, 2 pages.
Khan, Ikseer Azam, 19th Century Matba Nizami Kanpur, vol. IV, TKDL Formulation ID BA4/1854C, 1872, p. 309.
Lalla et al., Management of Oral Mucositis in Patients with Cancer, Nor. Am. Dent. Clin, vol. 52, No. 1, Jan. 2008, 17 pages.
Lednicky et al., Polyomaviruses and Human Tumors: A Brief Review of Current Concepts and Interpretations, Frontiers in Bioscience, vol. 4, Feb. 15, 1999, pp. 153-164.
Lee et al., Effects of Natural Products on the Inhibition of 5a-Reductase Type 2 for the Development of Chemopreventive Agents in LNCaP Cells, Natural Product Sciences, vol. 5, No. 2, 1999, pp. 97-103.
Lee et al., α- and β-Santalols Directly Interact with Tubulin and Cause Mitotic Arrest and Cytotoxicity in Oral Cancer Cells, Journal of Natural Products, vol. 78, No. 6, Jun. 26, 2015, pp. 1357-1362.
Moonen et al., Human Papilloma Virus DNA and p53 Mutation Analysis on Bladder Washes in Relation to Clinical Outcome of Bladder Cancer, European Eurology, vol. 52, No. 2, Aug. 2007, pp. 464-469.
Panda, The Complete Technology Book on Herbal Perfumes & Cosmetics, National Institute of Industrial Research, 2003, 4 pages.
Piggott et al., Western Austrian Sandalwood Oil Extraction by Different Techniques and Variations of the Major Components in Different Sections of a Single Tree, Flavour and Fragrance Journal, vol. 12, 1997, pp. 43-46.
Raju et al., Formulation and Evaluation of Oral and Topical Preparations Using Natural Products, Journal of Natural Pharmaceuticals, vol. 4, No. 1, 2013, pp. 37-47.
Sahib, Anuboga Vaithya Navaneetham, Part 6, Ed: Mohammed Abdulla Shahib, Publisher: Thamarai Noolagam, Chennai, 2001, pp. 47-48.
Sindhu et al., Santalum Album Linn: A Review on Morphology, Phytochemistry and Pharmacological Aspects, International Journal of PharmTech Research, vol. 2, No. 1, Jan. 2010, pp. 914-919.
Takatsuki et al., Studies on Cytotoxic Activity of Animal and Plant Crude Drugs, Natural Medicines, vol. 50, No. 2, 1996, pp. 145-157.
Vaidya, Asava Vijnan, Translated by Swami Harisaranananda Vaidya, published by The Punjab Ayurvedic Pharmacy, Amritsar, 3rd edition, 2000, 4 pages.
Vettian, 10-15th Century A.D., Ed: Mangadu Vadivel Mudalia, Pub: Parthina Nayakar & sons, Thirumagal Vilakku press, Chennai, TKDL identifier GP11/20, 2013, pp. 272-278.
EP16854327.0, "Office Action", dated Apr. 22, 2020, 4 pages.
Ha et al., "A phase II, proof-of-concept pilot clinical study of a mouth rinse containing sandalwood album oil (SAO) for the prevention of oral and oropharyngeal mucositis associated with (Chemo-)radiation therapy in head and neck cancer patients", J Clin Radiat Oncol. 3(1):1-5, Feb. 28, 2020.
"A Mouth Rinse Containing East Indian Sandalwood Oil (EISO) for the Prevention and Treatment of Oral Mucositis", History of Changes for Study: NCT02399228, vol. 2, Available online at: https://clinicaltrials.gov/ct2/history/NCT02399228?V_2=View#StudyPageTop>, Jul. 21, 2015, 4 pages.
Application No. JP2018-517788, Office Action, dated Sep. 4, 2020, 9 pages.
Takahata et al., "Estimated Daily Intake of Preservatives (Benzoic Acid, Parabens) Contained in Mouthwash and Liquid Toothpaste", Journal of Japanese Society of Food Chemistry, vol. 17, No. 3, 2010, pp. 221-226.

\* cited by examiner

SANDALWOOD OIL AND ITS USES RELATED TO ORAL MUCOSITIS

This application claims the benefit of U.S. Provisional Application No. 62/238,449, filed Oct. 7, 2015, which is hereby incorporated herein in its entirety.

BACKGROUND

Oral mucositis is an inflammation of the oral mucosa that is often a debilitating complication of cancer treatment. Therefore, methods of treating or preventing oral mucositis are necessary.

SUMMARY

Provided herein are methods of using therapeutically effective compositions of sandalwood oil to treat or prevent oral mucositis. Also provided are methods of making and using the compositions. More specifically, provided herein is a method of treating or preventing oral mucositis in a subject by administering to the subject a composition including a therapeutically effective amount of sandalwood oil.

DETAILED DESCRIPTION

In the present methods, oil from any member of the genus *Santalum* can be used. For example, and not to be limiting, East Indian sandalwood (*Santalum album*) or West Australian sandalwood (*Santalum spicatum*) can be utilized in the methods set forth herein. Several other species of the genus also have fragrant wood and are found across India, Australia, Indonesia, and the Pacific Islands. For example, *Santalum ellipticum, S. freycinetianum*, and *S. paniculatum*, the Hawaiian sandalwoods, can also be used.

By way of example, *Santalum album* (East Indian sandalwood) is useful in methods and compositions for treating oral mucositis. Other species produced in Australia that can be utilized in the methods and compositions set forth herein include, but are not limited to, *S. acuminatum, S. lanceolatum, S. murrayanum, S. obtusifolium* and *S. spicatum*. The compositions set forth herein can comprise one or more sandalwood oils. The oil(s) can be from one or more members of the genus *Santalum*.

The components of *S. spicatum* and *S. album* species are different. A comparison of the components of steam distilled West Australian and East Indian sandalwood heartwood oils is presented in Table 1. The components and their percentages can vary with the method of production.

TABLE 1

Typical Sandalwood Heartwood Oil Profiles

| Compound | S. spicatum | S. album |
|---|---|---|
| E nerolidol | 2.1% | 0.1% |
| Alpha-santalene | nd | 0.5% |
| Cis-alpha-(trans) bergamotene | nd | 0.7% |
| Epi-beta-santalene | nd | 1.1% |
| Beta-santalene | nd | 0.3% |
| Gamma-curcumene | nd | 0.2% |
| Dendrolasin | 1.2% | 0.2% |
| Alpha-santalol | 17.2% | 48.7% |
| Beta-bisabolol | 2.3% | 0.5% |
| Epi-alpha-bisabolol | 8% | nd |
| Z-alpha trans-bergamotol | 4.2% | 2.4% |
| Epi beta-santalol | 1.2% | 5% |
| Cis-beta-santalol | 11.4% | 20.4% |
| E,E,farnesol | 6.5% | nd |
| Cis nuciferol | 13.5% | 0.6% |
| Z-beta-curcumen-12-ol | 7.9% | 0.2% |
| cis lanceol | 2.9% | 1.5% |

The sandalwood heartwood oil can be prepared by steam distillation, supercritical $CO_2$ extraction, solvent extraction, hydro-distillation and combinations thereof. The sandalwood heartwood oil can also be double distilled. It is also possible to synthesize one or more of the active ingredients of sandalwood heartwood oil, as identified in Table 1, and thereafter combine individual active ingredients together.

As used herein, a sandalwood heartwood oil can be a sandalwood heartwood oil that conforms with International Organization for Standardization (ISO) specifications for the oil and therefore comprises 20-45% santalols, when derived from *S. spicatum*, and 57-79% santalols when derived from *S. album*. However, the 20-45% santalols from *S. spicatum* and the 57-79% santalols from *S. album* are determined against the pure oil and before such oil is combined with any other solvents, excipients or active ingredients. It is understood that an efficacious preparation of sandalwood heartwood oil may have a concentration of santalols lower (or higher) than the sandalwood heartwood oil it is prepared from and that the efficacious concentrations may be derived from sandalwood heartwood oils that are outside of the ISO specification prior to formulation. A santalol can be an α-santalol (shown below), a β-santalol (shown below), or any other active isomers or derivatives (such as esters) thereof.

As used herein, a sandalwood heartwood oil can comprise at least about 20%, 25%, 30%, 35%, 40%, 45%, 50%, 55%, 60%, 65%, 70%, 75%, 80%, 85%, 90%, 95%, 99% santalols or any percentage in between the percentages set forth herein, when derived from *S. spicatum*. The sandalwood heartwood oil can comprise at least 45%, 50%, 55%, 60%, 65%, 70%, 75%, 80%, 85%, 90%, 95%, 99% santalols or any percentage in between the percentages set forth herein, when derived from *S. album*. As set forth above, the oil can be extracted from cultivated trees or from an oil-producing cell culture.

In the methods and compositions set forth herein, the sandalwood heartwood oil can comprise the ingredients in the amounts listed in Table 1 plus or minus about 20%, and more preferably plus or minus about 10%, 5%, 2%, 1% or any percentage in between 0 and 20%.

It is also understood that the activity of sandalwood heartwood oil can be due to one or more components set forth in Table 1 acting either separately or together. Therefore, formulations that increase the concentration of the active component(s) and reduce the concentration of the inactive component(s) are set forth herein. Synthetic versions of the active components, or their derivatives, may be formulated in conjunction with or to replace the naturally occurring components of sandalwood heartwood oil. Compositions comprising purified or synthetic versions of an active component or derivative thereof can also be utilized in the methods set forth herein. For example, a composition comprising alpha-santalol (shown below) or beta-santalol (shown below) can be utilized to treat or prevent oral mucositis.

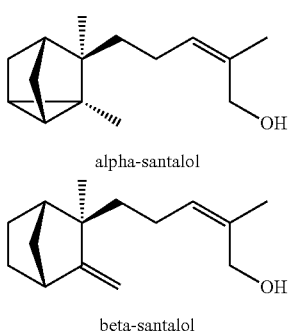

alpha-santalol beta-santalol

The therapeutically effective amount of sandalwood heartwood oil utilized in the compositions set forth herein can be, for example, a concentration greater than about 0.02% (w/w) and up to about 100% (w/w). For example, the therapeutically effective amount can be about 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10.0%, 15%, 20%, 25%, 30%, 35%, 40%, 45%, 50%, 55%, 60%, 65%, 70%, 75%, 80%, 85%, 90%, 95%, 100% or any percentage (w/w) in between the percentages set forth herein.

Provided herein is a method of treating or preventing oral mucositis in a subject. The method comprises administering to the subject a composition comprising a therapeutically effective amount of sandalwood oil. Optionally, the subject has cancer.

Oral mucositis is an inflammation of oral mucosa often resulting from treatment with chemotherapeutic agents or radiation. Oral mucositis can cause pain, mouth ulcers, erythema and/or difficulty swallowing. As a result of cell death in reaction to chemotherapy or radiotherapy, the mucosal lining of the mouth becomes thin, may slough off and then become red, inflamed and ulcerated. The ulcers can become covered with a yellowish white fibrin clot called a pseudomembrane. Ulcers can range from about 0.5 cm to greater than 4 cm. Further, the inflammatory response can cause pain and discomfort that result in dysphagia and odynophagia, excessive secretions and associated nausea. The degree of pain is usually related to the extent of the tissue damage and patients often require a temporary feeding tube to go through radiotherapy.

Dysgeusia, or an alteration in taste perception, can also occur, especially for those who are receiving radiation therapy to the neck and mouth area. Oral mucositis also has a negative impact on patients' qualities of life and a concomitant lack of compliance with treatment resulting in radiation treatment breaks or discontinuation. Oral mucositis can also cause weight loss making radiation dose delivery less optimal, secondary to significant tissue volume changes.

The severity of oral mucositis can be evaluated using several different assessment tools. Two of the most commonly used are the World Health Organization (WHO) Oral Toxicity score http://en.wikipedia.org/wiki/Mucositis—cite_note-7 (World Health Organization "Handbook for reporting results of cancer treatment. Geneva, Switzerland: World Health Organization 1979: 15-22) and the National Cancer Institute Common Toxicity Criteria (NCI-CTC) for Oral Mucositis (National Cancer Institute Common Toxicity Criteria Manual Version 2.0, Jun. 1, 1999). The Oral Mucositis Assessment Scale (OMAS) was developed in 1999. This scale has been shown to be highly reproducible between observers, responsive over time, and accurate in recording symptoms associated with mucositis. The OMAS provides an objective assessment of oral mucositis based on assessment of the appearance and extent of redness and ulceration in various areas of the mouth (See Sonis et al. "Validation of a new scoring system for the assessment of clinical trial research of oral mucositis induced by radiation or chemotherapy. Mucositis Study Group. *Cancer.* 1999; 85: 2103-2113).

As used herein, a subject can be a vertebrate, more specifically a mammal (e.g., a human, horse, pig, rabbit, dog, sheep, goat, non-human primate, cow, cat, guinea pig or rodent), a bird, a reptile or an amphibian. The term does not denote a particular age or sex. Thus, adult and newborn subjects, whether male or female, are intended to be covered. As used herein, patient or subject may be used interchangeably and can refer to a subject with a disease or disorder. The term patient or subject includes human and veterinary subjects.

As used herein, cancer is a disease in which the cells proliferate more rapidly than normal tissue growth. Cancer can be a neoplasm, also referred to as a tumor. A neoplasm can include, but is not limited to, pancreatic cancer, bladder cancer, head and neck cancer, melanoma, endometrial cancer, ovarian cancer, uterine cancer, non-Hodgkin lymphoma, breast cancer, brain cancer (e.g., glioblastoma), lung cancer, prostate cancer, colorectal cancer, thyroid cancer, renal cancer, adrenal cancer, liver cancer, neurofibromatosis, and leukemia. A neoplasm can be a solid neoplasm (e.g., sarcoma or carcinoma) or a cancerous growth affecting the hematopoietic system (e.g., lymphoma or leukemia).

A subject at risk of developing oral mucositis is an individual undergoing or about to undergo treatment for cancer. Such treatment includes chemotherapy, radiation therapy (especially for head and neck cancer) or stem cell transplant.

As used herein the terms treatment, treat, treating or ameliorating refers to a method of reducing one or more signs or symptoms of the disease or condition. Thus, in the disclosed methods, treatment can refer to a 10%, 20%, 30%, 40%, 50%, 60%, 70%, 80%, 90%, or 100% reduction or amelioration in the severity of an established disease or condition, as evidenced by a reduction in one or more signs or symptoms of the disease or condition. Examples of signs or symptoms of oral mucositis include, but are not limited to, inflammation, ulcers, pain and erythema. For example, and not to be limiting, a method for treating oral mucositis is considered to be a treatment if there is at least a 10% reduction in one or more signs or symptoms of oral mucositis in a subject as compared to control. For example, the method for treating oral mucositis is considered to be a treatment if there is a 10% reduction in one or more signs or symptoms of oral mucositis (e.g., the size or number of ulcers) in a subject as compared to a control subject that did not receive a composition comprising sandalwood oil described herein. Thus the reduction can be a 10, 20, 30, 40, 50, 60, 70, 80, 90, 100%, or any percent reduction in between 10 and 100 as compared to control levels. It is understood that treatment does not necessarily refer to a cure or complete ablation of the disease, condition, or symptoms of the disease or condition.

As utilized herein, by prevent, preventing, or prevention is meant a method of precluding, delaying, averting, obviating, forestalling, stopping, or hindering the onset, incidence, severity, or recurrence of oral mucositis. For example, the disclosed method is considered to be a prevention if there is a reduction or delay in onset, incidence, severity, or recurrence of oral mucositis or one or more symptoms of oral mucositis (e.g., ulcers, pain or difficulty swallowing) in a subject susceptible to oral mucositis as compared to control subjects susceptible to oral mucositis that did not receive a composition comprising sandalwood oil described herein. The disclosed method is also considered to be a prevention if there is a reduction or delay in onset, incidence, severity, or recurrence of oral mucositis or one or more symptoms of oral mucositis in a subject susceptible to oral mucositis after receiving a composition comprising sandalwood oil described herein, as compared to the subject's progression prior to receiving treatment. Thus, the reduction or delay in onset, incidence, severity, or recurrence of oral mucositis can be about a 10, 20, 30, 40, 50, 60, 70, 80, 90, 100%, or any amount of reduction in between.

For the administration methods disclosed herein, each method can optionally comprise the step of diagnosing a subject with oral mucositis or at risk of developing oral mucositis. The method can also include assessing the effectiveness of the sandalwood oil composition and modifying the treatment regimen. The method optionally includes modifying the treatment, for example, by adjusting the concentration or frequency of administration of sandalwood oil or providing a combination of treatments, as described below.

The compositions set forth herein can be provided in a pharmaceutical composition. The compositions include a therapeutically effective amount of the sandalwood oil in combination with a pharmaceutically acceptable carrier and, in addition, may include other medicinal agents, pharmaceutical agents, carriers, or diluents. Depending on the intended mode of administration, the pharmaceutical composition can be in the form of solid, semi-solid or liquid dosage forms, such as, for example, tablets, pills, lozenges, capsules, powders, liquids (e.g. a mouthwash), or suspensions, preferably in unit dosage form suitable for single administration of a precise dosage.

It is understood that the terms mouthwash, mouth rinse and oral rinse are interchangeable. The mouthwash compositions described herein can comprise sandalwood oil in an amount of about 0.03% to about 10% of the total weight of the mouthwash composition. For example, the amount of sandalwood can be from about 0.03% to about 0.25%, from about 0.03% to about 0.5%, from about 0.03% to about 1%, from about 0.03% to about 2%, from about 0.03% to about 3%, from about 0.03% to about 4%, from about 0.03% to about 5%, from about 0.03% to about 6%, from about 0.03% to about 7%, from about 0.03% to about 8%, from about 0.03% to about 9%, from about 0.03% to about 10% or any percentage in between the percentages set forth herein. In addition to sandalwood oil, the mouthwash compositions can further comprise other fragrant essential oils such as spearmint oil or peppermint oil. Optionally, the amount of the additional essential oils can be from about 0.025% to about 0.5% of the total weight of the mouthwash composition. For example, the amount of one or more essential oils can be from about 0.025% to about 0.1%, from about 0.025% to about 0.2%, 0.025% to about 0.3%, 0.025% to about 0.4%, 0.025% to about 0.5%, or any percentage in between the percentages set forth herein. The mouthwash composition can further comprise one or more surfactants. Optionally, the amount of the surfactant(s) can be from about 1% to about 15% of the total weight of the mouthwash composition. One or more sweeteners, colorants and preservatives can also be included in the mouthwash compositions of the present invention. Preservatives that can be used in the compositions set forth herein include, but are not limited to, benzoic acid, sodium benzoate, citric acid, an acetate buffer, chlorhexidine, parabens, triclosan and potassium sorbate. The concentration of each preservative or a combination of one or more preservatives can be about 0.01% to about 10% (w/w). For example, the concentration of the preservative can be about 0.01% to about 0.1% (w/w), from about 0.01% to about 0.2% (w/w), from about 0.01% to about 0.3% (w/w), from about 0.01% to about 0.4% (w/w), from about 0.01% to about 0.5% (w/w), from about 0.01% to about 0.6% (w/w), from about 0.01% to about 0.7% (w/w), from about 0.01% to about 0.8% (w/w), from about 0.01% to about 0.9% (w/w), from about 0.01% to about 1.0% (w/w), from about 0.1% to about 1%, from about 0.2% to about 1%, from about 0.3% to about 1%, from about 0.4% to about 1%, from about 0.5% to about 1%, from about 0.6% to about 1%, from about 0.7% to about 1%, from about 0.8% to about 1%, from about 0.9% to about 1%, from 0.1% to about 2%, from 0.1% to about 3%, from 0.1% to about 4%, from 0.1% to about 5%, from 0.1% to about 6%, from 0.1% to about 7%, from 0.1% to about 8%, from 0.1% to about 9%, from 0.1% to about 10%.

The pH of the mouthwash composition can be optimized to treat oral mucositis in a subject and inhibit microbial growth in the mouthwash composition. Optionally, the pH of the mouthwash composition can be a pH of less than about 7. For example, the pH can be from about 2.5 to about 6.5, from about 2.5 to about 4.5, from about 2.5 to about 4.0, from about 2.5 to about 3.5, or from about 2.5 to about 3.0. The pH of the mouthwash composition can also be a pH of about 3.5 to about 6.5, from about 3.5 to about 6.0, from about 3.5 to about 5.5, from about 3.5 to about 5.0, about 3.5 to about 4.5, or from about 3.5 to about 4.0. The pH of the mouthwash composition can also be a pH of about 4.0 to about 6.5, from about 4.0 to about 6.0, from about 4.0 to about 5.5, from about 4.0 to about 5.0, or from about 4.0 to about 4.5. The pH of the mouthwash composition can also be a pH of about 4.5 to about 6.5, from about 4.5 to about 6.0, from about 4.5 to about 5.5, or from about 4.5 to about 5.0. The pH of the mouthwash composition can also be a pH of about 5.0 to about 6.5, from about 5.0 to about 6.0, or from about 5.0 to about 5.5. The pH of the mouthwash composition can also be a pH of about 5.5 to about 6.5 or from about 5.5 to about 6.0. Optionally, the mouthwash compositions provided herein are alcohol-free.

Optionally, the composition is not in the form of a gel. By pharmaceutically acceptable is meant a material that is not biologically or otherwise undesirable, which can be administered to an individual along with sandalwood oil without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington: The Science and Practice of Pharmacy 22d edition Lloyd V. Allen et al., editors, Pharmaceutical Press (2012).

Examples of physiologically acceptable carriers include buffers such as phosphate buffers, citrate buffer, and buffers with other organic acids; saline solutions; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS (BASF; Florham Park, N.J.).

Compositions containing the agent(s) described herein suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

Liquid dosage forms for oral administration of the compositions described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, sesame oil, glycerol, tetrahydrofurfuryl alcohol, polyethylene glycols, and fatty acid esters of sorbitan, or mixtures of these substances, and the like. Besides such inert diluents, the composition can also include additional agents, such as wetting, emulsifying, suspending, sweetening, flavoring, or perfuming agents. The liquid dosage forms can also contain one or more surfactants. Also provided herein are liquid dosage forms that that do not contain alcohol, i.e., non-alcoholic liquid dosage forms.

The amount of therapeutic agent effective in treating oral mucositis can depend on the type of cancer and/or the type of chemotherapy and/or radiation therapy administered to the subject. This amount can be determined by standard clinical techniques. Therefore, these amounts will vary. The precise dose to be employed in the formulation will also depend on the seriousness of the disease or disorder and should be decided according to the judgment of the practitioner and each subject's circumstances.

The compositions comprising a therapeutically effective amount of sandalwood oil can be administered to the subject prior to, concurrently with (i.e., at the same time and/or in the same composition) or subsequent to administration of another pharmaceutical agent or agents. For example, a composition comprising a therapeutically effective amount of sandalwood oil can be administered to the subject prior to, concurrently with or subsequent to administration of an antimicrobial composition, an antifungal composition, an analgesic and/or an antifibrinolytic agent.

Examples of antimicrobial compositions include antibacterial and antifungal compositions (for example, amphotericin, fluconazole, nystatin and clortrimazole). Antiviral compositions can also be administered. Examples of analgesics include, but are not limited to, anti-inflammatory agents (for example, non-steroidal anti-inflammatory drugs (NSAIDS)), steroids, lidocaine, topical morphine, opioid drugs, doxepin rinse, benzydamine HCl topical rinse, benzocaine spray/gel, dyclonine rinse, diphenhydramine solution, Gelclair® (Lugano, Switzerland) and Caphosol® (Dublin, Ireland), to name a few. Examples of antifibrinolyic agents include, but are not limited to thrombin packs and topical agents such as tranexamic acid. The pharmaceutical agent can be formulated with the therapeutically effective amount of sandalwood in a single composition or can be formulated in a separate composition.

A coating agent comprising a therapeutically effective amount of sandalwood oil and/or an analgesic can also be administered. Coating agents include, but are not limited to milk of magnesia, kaolin with pectin suspension, mixtures of aluminum, and magnesium hydroxide suspensions.

It is understood that any of the compositions comprising a therapeutically effective amount of sandalwood oil can be administered to the subject prior to, concurrently with or subsequent to radiation therapy and/or chemotherapy. The subject undergoing radiation therapy and/or chemotherapy can be a subject that has undergone or will undergo a stem cell transplant.

Any appropriate route of administration may be employed, for example, administration can be systemic or local. Systemic administration includes administration via injection or infusion. Routes of administration include, but are not limited to, parenteral, intravenous, subcutaneous, intramuscular, intraventricular, intracorporeal, intraperitoneal and oral administration. Pharmaceutical compositions can be delivered locally to the area in need of treatment, by topical application or local injection to the surface of mucous membranes, for example, to the mouth of a subject. The composition can be applied in any form suitable for topical administration, for example, a gel, suspension, cream, ointment, foam, spray or mouthwash, to name a few. A medicinal gauze or mesh comprising a composition described herein can also be directly applied to the mouth of the subject.

Ranges may be expressed herein as from about one particular value, and/or to about another particular value. When such a range is expressed, this includes from the one particular value and/or to the other particular value. Similarly, when values are expressed as approximations, by use of the antecedent about, it will be understood that the particular value is disclosed.

Throughout this application, various publications are referenced. The disclosures of these publications in their entireties are hereby incorporated by reference into this application.

A number of aspects have been described. Nevertheless, it will be understood that various modifications may be made. Furthermore, when one characteristic or step is described it can be combined with any other characteristic or step herein even if the combination is not explicitly stated. Accordingly, other aspects are within the scope of the claims.

EXAMPLES

The following is a non-limiting example of a composition (Formulation A) that can be used to treat oral mucositis. This formulation was tested for preservative efficacy. As set forth in Table 2, a sample of the formulation was inoculated with the specified concentrations (cfu/ml) of microorganisms. As shown in table 2, the sample of Formulation A (pH 4.0) passed the United States Pharmacopeia requirements for antimicrobial preservative effectiveness as no significant microbial growth was detected in the sample at fourteen or twenty-eight days after inoculation. However, when a sample of Formulation A (pH of 6.9) was tested for antimicrobial preservative effectiveness, microbial growth was detected in the sample at fourteen or twenty-eight days after inoculation.

Formulation A

| Components | Mouth Rinse Alcohol-Free % (w/w) |
| --- | --- |
| Rectified East Indian Sandalwood Oil (EISO) | 0.25 |
| Polysorbate-80, NF | 7 |
| Poloxamer 407, NF | 2 |
| Xylitol, NF | 5 |
| Sorbitol 70% Solution, USP | 5 |
| Menthol, USP | 0.1 |
| Peppermint Oil, NF | 0.1 |
| Sodium Saccharin, USP | 0.03 |
| Glycerin, USP | 2.0 |
| Xanthan Gum, NF | 0.2 |
| Benzoic Acid | 0.2 |
| Thymol | 0.03 |
| Purified Water, USP | QS |
| pH | ~4.0 |

TABLE 2

| Organisms | Inoc. Level | Day: 14 Mar. 3, 2015 | Day: 28 Mar. 17, 2015 | Pass/Fail |
| --- | --- | --- | --- | --- |
| E. coli (ATCC 8739) | $5.71 \times 10^5$ | <1 | <1 | PASS |
| S. aureus (ATCC 6538) | $4.61 \times 10^5$ | <1 | <1 | PASS |
| P. aeruginosa (ATCC 9027) | $4.01 \times 10^5$ | <1 | <1 | PASS |
| C. albicans (ATCC 10231) | $7.21 \times 10^5$ | <1 | <1 | PASS |
| A. brasilliensis (ATCC 16404) | $3.25 \times 10^5$ | 27 | 18 | PASS |

The following are additional non-limiting examples of compositions (Formulations B through G) that can be used to treat oral mucositis. These formulations were tested for preservative efficacy. A sample of each formulation was inoculated with the concentrations (cfu/ml) of microorganisms as set forth above in Table 2. As shown in Table 3, the sample of Formulation B (pH 4.0), the sample of Formulation D (pH 4.0), the sample of Formulation E (pH 3.5), the sample of Formulation F (pH 4.3) and the sample of Formulation G (pH 4.1) passed the United States Pharmacopeia requirements for antimicrobial preservative effectiveness as no significant microbial growth was detected in the sample at fourteen or twenty-eight days after inoculation. However, when a sample of Formulation C (pH of 6.0) was tested for antimicrobial preservative effectiveness, microbial growth was detected in the sample at fourteen or twenty-eight days after inoculation.

TABLE 3

| Components | 15-0507-01 Formulation B | 15-0507-02 Formulation C | 15-0512-01 Formulation D | 15-0522-04 Formulation E | 15-0522-05 Formulation F | 15-0522-06 Formulation G |
| --- | --- | --- | --- | --- | --- | --- |
| Rectified East Indian Sandalwood Oil (EISO) | 0.25 | 0.25 | 0.25 | 0.25 | 0.25 | 0.25 |
| Polysorbate-80, NF | 7 | 7 | 7 | 7 | 7 | 7 |
| Poloxamer 407, NF | 2 | 2 | 2 | 2 | 2 | 2 |
| Xylitol, NF | 5 | 5 | 5 | 5 | 5 | 5 |
| Sorbitol 70% Solution, USP | 5 | 5 | 5 | 5 | 5 | 5 |
| Menthol, USP | 0.1 | 0.1 | 0.1 | 0.1 | 0.1 | N/A |
| Peppermint Oil, NF | 0.1 | 0.1 | 0.1 | 0.1 | 0.1 | 0.25 |
| Sodium Saccharin, USP | 0.03 | 0.03 | 0.03 | 0.03 | 0.03 | 0.03 |
| Glycerin, USP | 2 | 2 | 2 | 2 | 2 | 2 |
| Xanthan Gum, NF | 0.2 | 0.2 | 0.2 | 0.2 | 0.2 | 0.2 |
| Benzoic Acid, USP | 0.2 | N/A | 0.2 | N/A | N/A | 0.2 |
| Acetate Buffer | N/A | N/A | N/A | N/A | Sodium Acetate 0.12% Acetic Acid 0.18% | N/A |
| Citric Acid, USP | N/A | N/A | N/A | 0.1 | N/A | N/A |
| Purified Water, USP | QS | QS | QS | QS | QS | QS |
| Target pH | ~4.0 | 6.0 | 4.0 | 3.5 | 4.3 | 4.1 |
| Challenge Results | Pass | Fail | Pass | Pass | Pass | Pass |
| Organism | A. brasiliensis < 1,350 | A. brasiliensis < 37,000 E. coli & P. aeruginosa Fail | A. brasiliensis < 550 | A. brasiliensis < 28,600 | A. brasiliensis < 1 | A. brasiliensis < 850 |

Treatment of Oral Mucositis

Subjects with head and neck cancer involving the oropharynx or oral cavity, who are expected to undergo high dose radiation therapy (i.e., ≥60 Gy) that typically results in oral mucositis, with or without concurrent chemotherapy or biologic targeted therapy will be selected. These subjects will not have preexisting mucositis from other causes, be immunosuppressed or chronically using immunosuppressive drugs. Further, these subjects will have had no prior radiation therapy to the head and neck area, and no chemotherapy within the last year except for induction chemotherapy delivered (or to be delivered) prior the current course of radiation therapy.

Once subject eligibility is confirmed, subjects will start treatment for oral mucositis on Day 1 of their radiation treatment. All subjects will receive Formulation A at the clinic, with the first dose administered on Day 1. A baseline measurement of mouth pain and pain with swallowing, according to the Numerical Rating Pain Scale will be obtained on Day 1.

Subjects will take about 15 ml of Formulation A by mouth, swish for about thirty seconds, gargle and spit. The 15 ml of Formulation A can be taken as a single bolus or portions thereof, in series. For example, the subject can take about 7.5 ml of Formulation A by mouth, swish for about thirty seconds, gargle, spit and repeat taking about 7.5 ml of Formulation A by mouth, swish for about thirty seconds, gargle, and spit. In other words, the subject can take 7.5 ml of Formulation A by mouth, swish for about thirty seconds, gargle and spit, twice per treatment. Alternatively, the subject can (1) take about 5 ml of Formulation A by mouth, swish for about thirty seconds, gargle and spit; (2) repeat taking about 5.0 ml of Formulation A by mouth, swish for about thirty seconds, gargle and spit; and (3) repeat taking about 5.0 ml of Formulation A by mouth, swish for about thirty seconds, gargle and spit. In other words, the subject can take 5.0 ml of Formulation A by mouth, swish for about thirty seconds, gargle and spit, thrice per treatment.

Each treatment will be performed thrice daily, including weekends when radiotherapy is not delivered, ideally 15 minutes after meals or at least one hour before eating or drinking until oral mucositis resolves.

Subjects will return to the clinic once a week while receiving radiation and then once every two weeks once their radiation has been completed and then until their mucositis has resolved for the final visit. During each visit, a Numerical Rating Pain Scale measurement, as related to mouth pain and pain with swallowing will be obtained. The oral cavity will also be inspected and mucositis will be graded according to the following Radiation Therapy Oncology Group (RTOG) grading scale for acute radiation mucositis.

| Radiation Therapy Oncology Group (RTOG) grading scale | |
| --- | --- |
| Grade | Mucous Membrane |
| 0 | No change over baseline |
| 1 | Injection/may experience mild pain not requiring analgesic |
| 2 | Patchy mucositis which may produce an inflammatory serosanguinitis discharge/may experience moderate pain requiring analgesia |
| 3 | Confluent fibrinous mucositis/may include severe pain requiring narcotic |
| 4 | Ulceration, hemorrhage or necrosis |

Primary efficacy will be assessed by the Numerical Rating Pain Scale and the Radiation Therapy Oncology Group mucositis grade at week 5. Additional secondary efficacy evaluations will include the severity of pain rated by the Numerical Rating Pain Scale and mucositis grade by Radiation Therapy Oncology Group criteria at each study visit, frequency of the percutaneous endoscopic gastrostomy tube for feeding during the duration of treatment and weight loss from baseline through weeks 5 and 7. Treatment is considered effective if a decrease in mouth pain and/or pain with swallowing, as measured by the Numerical Rating Pain Scale, occurs. Treatment is also considered effective if there is an improvement in mucositis as measured by the RTOG grading scale.

What is claimed is:

1. A method of treating oral mucositis in a subject, said method comprising administering to the subject in need thereof, a composition comprising about 0.03% to about 30% sandalwood oil (w/w), wherein the pH of the composition is about 3.5 to about 4.1, wherein the subject has head and neck cancer, and wherein the oral mucositis is caused by radiation therapy and/or chemotherapy.

2. The method of claim 1, wherein the composition is administered to the subject prior to, concurrently with, or subsequent to radiation therapy and/or chemotherapy.

3. The method of claim 1, wherein the composition is administered topically to the subject.

4. The method of claim 3, wherein the composition is administered topically to the mouth and/or throat of the subject.

5. The method of claim 4, wherein the composition is a mouthwash composition.

6. The method of claim 5, wherein the mouthwash composition is a non-alcoholic mouthwash composition.

7. The method of claim 1, wherein the sandalwood oil is from *Santalum album* or *Santalum spicatum* or a combination thereof.

8. The method of claim 1, wherein the composition further comprises a pharmaceutically acceptable carrier.

9. The method of claim 1, further comprising administering an antifungal composition, an analgesic, and/or an antifibrinolytic agent to the subject.

10. The method of claim 9, wherein the antifungal composition, the analgesic, and/or the antifibrinolytic agent are administered topically to the subject.

* * * * *